(12) United States Patent
Georg et al.

(10) Patent No.: US 7,660,624 B2
(45) Date of Patent: Feb. 9, 2010

(54) METHOD AND X-RAY SYSTEM FOR DETECTING POSITION CHANGES OF A MEDICAL IMPLANT

(75) Inventors: Christian Georg, Fronhausen (DE); Joachim Hornegger, Möhrendorf (DE); Klaus Jochen Klose, Fronhausen (DE); Volkmar Welker, Kirchhain (DE)

(73) Assignee: Siemens Aktiengesellschaft, Munich (DE)

( * ) Notice: Subject to any disclaimer, the term of this patent is extended or adjusted under 35 U.S.C. 154(b) by 792 days.

(21) Appl. No.: 10/822,382

(22) Filed: Apr. 12, 2004

(65) Prior Publication Data

US 2005/0020913 A1   Jan. 27, 2005

(30) Foreign Application Priority Data

Apr. 10, 2003   (DE)   ................. 103 16 558

(51) Int. Cl.
*A61B 5/05*   (2006.01)
(52) U.S. Cl. ................. 600/424; 600/407; 600/425; 600/426; 600/429; 382/128; 606/91; 424/423; 378/165; 378/62
(58) Field of Classification Search ................. 600/407, 600/410, 427, 425, 426, 429, 424; 606/61, 606/91; 382/128, 131, 132; 378/98.12, 165, 378/62; 424/423
See application file for complete search history.

(56) References Cited

U.S. PATENT DOCUMENTS

| | | | | |
|---|---|---|---|---|
| 4,349,498 A | * | 9/1982 | Ellis et al. ..................... 264/81 |
| 4,991,579 A | * | 2/1991 | Allen .......................... 600/426 |
| 5,676,146 A | * | 10/1997 | Scarborough ............... 600/431 |
| 6,701,174 B1 | * | 3/2004 | Krause et al. ............... 600/407 |
| 6,711,432 B1 | * | 3/2004 | Krause et al. ............... 600/427 |
| 6,723,097 B2 | * | 4/2004 | Fraser et al. .................. 606/61 |
| 6,811,310 B2 | * | 11/2004 | Lang et al. .................. 378/169 |
| 7,130,676 B2 | * | 10/2006 | Barrick ....................... 600/426 |
| 2001/0016203 A1 | * | 8/2001 | Lee et al. .................... 424/423 |
| 2001/0034480 A1 | * | 10/2001 | Rasche et al. ............... 600/407 |
| 2003/0112921 A1 | * | 6/2003 | Lang et al. .................... 378/54 |

* cited by examiner

*Primary Examiner*—Brian Casler
*Assistant Examiner*—Joel M Lamprecht
(74) *Attorney, Agent, or Firm*—Schiff Hardin LLP

(57) ABSTRACT

In a method and apparatus to detect position changes of an implant x-ray detectable markers are arranged in the environment of the implant, and 2D x-ray exposures are obtained at temporal intervals of a region containing the implant in which a distribution of the markers as well as of marked points of the implant are visible in each 2D x-ray exposure. A first of the 2D x-ray exposures is obtained at a first point in time from one projection direction, and a second of the 2D x-ray exposures is obtained at a second point in time from another projection direction. The distribution of the markers and marked points is determined in the first and second 2D x-ray exposure by an evaluation device, and from the distributions a degree of probability is calculated that the distribution of the first 2D x-ray exposure and the distribution of the second 2D x-ray exposure are projections of the same three-dimensional distribution of markers and marked points. An automated detection of position changes by implants with reduced x-ray exposure for the patient is facilitated.

12 Claims, 2 Drawing Sheets

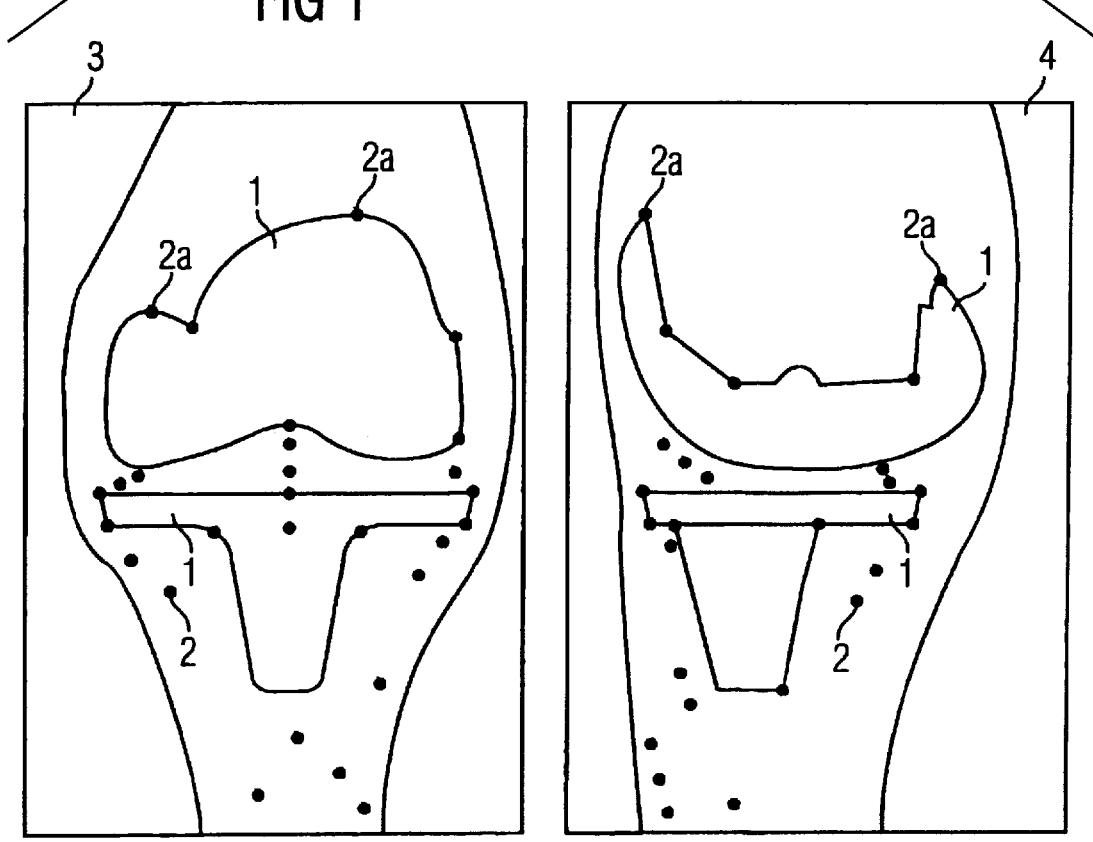
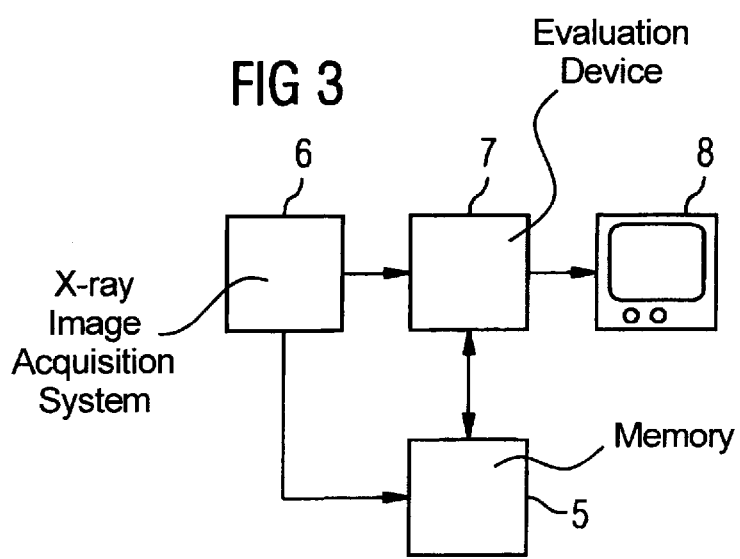

METHOD AND X-RAY SYSTEM FOR DETECTING POSITION CHANGES OF A MEDICAL IMPLANT

BACKGROUND OF THE INVENTION

1. Field of the Invention

The present invention concerns a method to detect position changes of a medical wherein x-ray detectable markers are arranged in the environment of the implant, and wherein a positional change of the implant is checked using 2D x-ray exposures at temporal intervals of a region containing the implant, using a distribution of the markers in each 2D x-ray exposure, with a first of the 2D x-ray exposures being obtained at a first point in time from one projection direction, and a second of the 2D x-ray exposures being obtained at a second point in time from another projection direction. The invention also concerns an x-ray system fashioned for implementation of the method.

2. Description of the Prior Art

Supervision of the change of the position of implants, in particular the position of implanted prostheses, is an important post-operative measure in order to be able to undertake timely corrections and to prevent complications. Immediately after the implantation of artificial joints, the prosthesis can loosen in the course of time due to weakening of the materials used. In order to recognize this loosening, in the implantation, in addition to the prosthesis, small metal spheres that can be clearly localized in x-ray exposures of this region are placed in the bones bordering the prosthesis. A shifting of the artificial joint relative to the bones can be detected in the x-ray exposure with these metal spheres serving as markers. Such a shifting is an indicator of the loosening of the artificial joint.

A known method for detection of the position change of an implant (as it is described, for example, in Selvik, G., Roentgen stereophotogrammetry, Acta Orthopaedica Scandinavica Supplementum No. 232, Volume 60, 1989, Reprint from the original 1971 thesis) requires the implementation of at least four x-ray exposures with a calibration pattern in order to be able to detect corresponding position changes. For this, at each of regular temporal intervals two 2D x-ray exposures of a region containing the implant are obtained together with the calibration pattern from two projection directions predetermined by the calibration pattern. Corresponding spheres as well as marked points of the implant in the exposures are respectively, manually marked in the 2D x-ray exposures acquired at each interval. With the help of these correspondences, the position of the spheres and marked points in the 2D x-ray exposures and the measurement data of the calibration pattern, a 3D model of the spheres in the bones as well as of the marked points of the implant is generated. The comparison of the 3D model calculated in this manner at each interval with a 3D model calculated earlier or later enables a decision as to whether a position change of the implant has occurred, and what dimension this position change exhibits. The comparison requires the consistent numbering of the individual points or spheres in the 2D x-ray exposures. The method is tedious and additionally stresses the patient with the x-ray dose applied in the x-ray exposures.

SUMMARY OF THE INVENTION

As used herein, "2D x-ray exposure" means an exposure in no more than two dimensions, i.e, it is not a part or subset of a 3D exposure.

An object of the present invention is to provide a method for fast and automatic recognition of position changes of an implant that subjects the patient to less radiation and that can be efficiently implemented.

This object is in accordance with the invention by a method to detect position changes of an implant, wherein which markers that are detectable in x-ray exposures are arranged in the environment of the implant and using 2D x-ray exposures of a region containing the implant obtained at temporal intervals, position changes of the implant are checked using a distribution of the markers as well as marked points of the implant in each 2D x-ray exposure. For this, a first of the 2D x-ray exposures is obtained at a first point in time from one projection direction, and a second of the 2D x-ray exposures is obtained at a second point in time from another projection direction. In both x-ray exposures, the distribution of the markers and marked points is determined in an evaluation device (that can be part of a data processing system) and calculated from the distributions a degree of probability that the distribution in the first 2D x-ray exposure and the distribution in the second 2D x-ray exposure are projections of the same three-dimensional distribution of markers and marked points. The marked points, for example, can be markers introduced in the implant and detectable in x-ray exposures, or can be edge or corner points, predetermined by the geometric shape of the implant, that can be unambiguously, spatially associated with the implant. Since, in the inventive method, the markers arranged in the environment of the implant essentially appear as points in the x-ray exposures, and in particular are evaluated as points, reference is made below to points as well as to a two- or three-dimensional distribution of points that encompasses the markers as well as the marked points of the implant.

Thus, in the present method a 3D model of the points is not calculated for each examination or measurement in order to then compare the models with one another. Instead, the present method functions with only one x-ray exposure in each examination. Only the probability or the degree of probability is calculated with which two different projections of the points (that are acquired from both of the 2D x-ray exposures acquired at different points in time as a distribution of the points) are projections of the same three-dimensional distribution of points. On the basis of this probability, a decision can then be made as to whether a position change, in particular a shifting of the implant between the two examinations, has occurred. Both x-ray exposures must be acquired from different projection directions in order to be able to detect a three-dimensional position change. A three-dimensional distribution of points need not be calculated, nor is a calibration pattern necessary for the detection of the position changes with the present method.

In contrast to known methods, the present method functions with only two x-ray exposures, such that the applied x-ray dose to the patient is halved. The method can be implemented very quickly and without user intervention by the automatic determination of the distribution of the points by the evaluation device and the calculation of the degree of probability based thereon.

In an embodiment of the present invention, a threshold of the degree of probability is predetermined, below which an indication notice of a position change is automatically generated, for example being output on a monitor. In this embodiment, the present method can be implemented completely automated, with only the result of the examination, as to whether a position change of the implant exists or not, being communicated to the user by the evaluation device. The method thus eases the necessary post-operative examinations and significantly reduces the time expenditure associated therewith for the user, as well as the costs associated therewith.

Thus, with the present method, the decision can be made automatically for the user as to whether a position change has occurred between two points in time or examinations, with each point in time respectively only one 2D x-ray exposure being obtained at a different viewing direction. A position change then is indicated based on a threshold set by the user for the degree of probability, when this threshold is not exceeded. The correspondences between the individual points of both x-ray exposures are automatically determined, possibly with manual correction entries. The absolute shifting of the points in three dimensions is not measured. The inventive method is based on an algorithm that calculates only whether two point quantities, the distributions of the markers and marked points represent, in two dimensions, the projection of the same 3D point quantity. The projection model used, perspective or parallel projection, naturally is taken into account in the algorithm. An example suitable for such an algorithm is described in J. Hornegger, V. Welker and H. Niemann, Localization and Classification Based on Projections, Pattern Recognition, 35:1225-1235, 2002. For the automatic determination of the distribution of the points in the individual x-ray exposures, as well as the determination of the correspondences, a digital image processing method is used it is known, for example, from "Introductory Techniques for 3-D Computer Vision" by Emanuele Trucco, Alessandro Verri; Prentice Hall; 1st edition (Mar. 6, 1998)/

The quantification of a detected position change of the implant cannot be effected directly with the present method. Should such a quantitative detection be necessary, basically two possibilities are available that require additional x-ray exposures or other imaging exposures of the region comprising the implant. In an embodiment, at least two calibrated 2D x-ray exposures from which, respectively, the 3D point quantities are reconstructed are made per examination, meaning both in the same session. The determination of the distribution of the points in the respective 2D x-ray exposures is likewise automatically implemented by the evaluation device. The position change can be quantitatively determined by comparison of the calibrated 3D point quantities of the temporally separated examinations. In a further embodiment, a 3D volume data set (that was acquired with a suitable 3D imaging method) of the region containing the implant can also be used to quantify the position change. This can ensue, for example, with a CT scan or an MR exposure. The shifting of the marked points or of the implant relative to the markers then can be quantitatively determined in three dimensions from this 3D volume data set.

The present method is in particular suited for detection of position changes of a prosthesis, with markers, as metal spheres being placed in a bone bordering the prosthesis. The shifting of joint prostheses then can be detected directly, very rapidly and with a lesser number of x-ray exposures.

In addition to the known components necessary for the acquisition, the present x-ray system to implement the method has an evaluation device for determining a distribution of markers and marked points in a 2D x-ray exposure and for calculating a degree of probability that two distributions from two 2D x-ray exposure are projections of the same three-dimensional distribution of markers and marked points.

DESCRIPTION OF THE DRAWINGS

FIG. 1 show an example for two 2D x-ray exposures with a distribution of markers, obtained from different directions in accordance with the invention.

FIG. 3 is a block diagram of the basic components of the inventive x-ray system.

DESCRIPTION OF THE PREFERRED EMBODIMENTS

Figure 2:
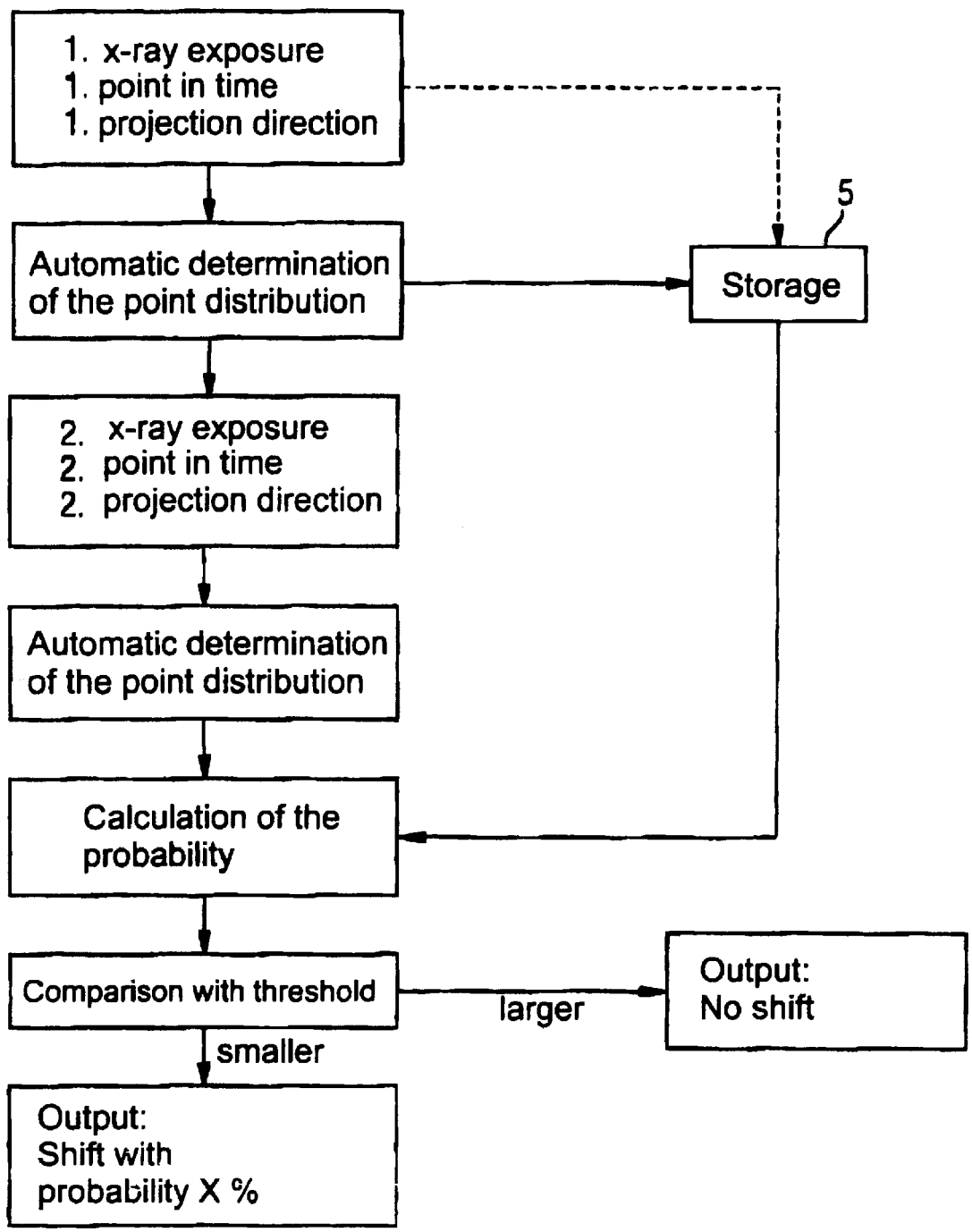
FIG. 2 is a flow chart for the implementation of the inventive method.

FIG. 1 shows an example two 2D x-ray exposures of a region containing an implant, in the present example a joint prosthetic 1 at the knee joint. The x-ray exposures were respectively obtained at different points in time from different directions, in the present example perpendicular to one another. In the x-ray exposures, respectively both components of the joint prosthetic 1 as well as metal spheres 2 (that are used as markers) placed in the bone are recognizable. Due to their placement in the bone, these metal spheres 2 do not change their position over the course of time. If a shifting of the joint prosthesis 1 occurs, this shifting can be recognized by a changed position of the prosthesis 1, or marked points 2a of the prosthesis 1, relative to the metal spheres 2 in the x-ray image.

In the inventive method, the distribution of the metal spheres 2 as well as marked points 2a are automatically determined both in the first x-ray exposure 3 and in the second x-ray exposure 4 by an image processing method. A suitable method for automatic detection of corners is described, for example, in Xintong Zhan, Dongming Zhao, A Parallel Algorithm for Detecting Dominant Points on Multiple Digital Curves, Pattern Recognition, Vol. 30, No. 2, pp. 239-244, 1997. This determination, as shown in the flow chart of FIG. 2, can ensue directly after the implementation of the respective x-ray exposure, whereby the distribution is then stored in a memory. The automatic determination of the distribution alternatively can first ensue after implementation of the second x-ray exposure, whereby the image data of the first x-ray exposure must then be stored in a memory.

In the present example, in which the x-ray exposures of an artificial knee joint and the markers in the bone are generated, there is a span of time of, for example, a few weeks between the two x-ray exposures 3 and 4 that are acquired from different projection directions. After the automatic detection of the distribution of the metal spheres 2 and marked points 2a in the x-ray exposures 3, 4, the degree of probability is calculated that the points corresponding to the metal spheres 2 and the marked points 2a in the two exposures are projections of the same 3D point configuration. If a selected threshold for the degree of probability is not exceeded, a shifting of the prosthesis 1 is then considered as very probable. In this case a notification of such a possible shifting of the prosthesis 1 is output by the evaluation device. In the other case, a notification of a probable position constancy of the prosthesis 1 is indicated.

FIG. 3 shows (in highly schematic form) the evaluation device 7 that is necessary in addition to the known x-ray image acquisition system 6 for the detection of the distribution of the points (2, 2a) in the 2D x-ray exposures as well as the calculation of the degree of probability and output of a calculation result to a monitor 8. The evaluation device 7 preferably is part of a data processing system of the x-ray system.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for detecting position changes of a medical implant in a patient, comprising the steps of:
   disposing a plurality of x-ray detectable markers in an anatomical environment of an implanted medical implant, said markers being spatially separated from said medical implant and said medical implant having x-ray detectable points thereon different from said markers;
   obtaining one first 2D x-ray exposure, from a first projection direction, of a region of the patient containing said implant and said anatomical environment at a first point in time, in which a first distribution of said markers and said points is detectable;
   obtaining one second 2D x-ray exposure, from a second projection direction different from said first projection direction, of said region at a second point in time, in which a second distribution of said markers and said points is detectable, said second point in time being temporally separated from said first point in time such that a positional change of said implant in said environment may have occurred;
   electronically detecting said first and second distributions respectively in said first and second 2D x-ray exposures; and
   in a processor, automatically calculating from said first and second distributions, with no 3D reconstruction of spatial positions of said markers and points, a degree of probability that said first and second distribution represent projections of the same three-dimensional distribution of said markers and said points and, from said degree of probability, determining whether a positional change of said implant in said environment has occurred and, from said processor, emitting an indication that identifies only whether said positional change has occurred or not occurred.

2. A method as claimed in claim 1 wherein the step of determining whether said positional change of the implant has occurred comprises defining a degree of probability threshold, and automatically electronically generating said indication that a positional change of said implant has occurred if said degree of probability does not exceed said threshold.

3. A method as claimed in claim 1 comprising detecting said first and second distributions by digital image processing of the respective first and second 2D x-ray exposures.

4. A method as claimed in claim 1 comprising:
   at said first point in time, also obtaining a first calibrated 2D x-ray exposure of said region;
   from said first 2D x-ray exposure and said first calibrated 2D x-ray exposure, calculating a first 3D distribution of said markers and points for said first point in time;
   at said second point in time, obtaining a second calibrated 2D x-ray exposure of said region;
   from said second 2D x-ray exposure and said second calibrated 2D x-ray exposure, calculating a second 3D distribution of said markers and said points for said second point in time; and
   comparing said first 3D distribution and said second 3D distribution and, from said comparison, calculating a magnitude of said positional change of said implant, if said position change has occurred.

5. A method as claimed in claim 1 wherein said implant is a prosthesis, and wherein the step of disposing a plurality of x-ray detectable markers in an anatomical environment of said implant comprises disposing a plurality of metal spheres in at least one bone bordering said prosthesis.

6. A method as claimed in claim 1 comprising designating said points of said implant by introducing x-ray detectable markers into said implant.

7. An x-ray system comprising:
   a medical implant having x-ray detectable points thereon, said medical implant being configured for implantation in a patient;
   a plurality of x-ray detectable markers configured to be disposed in an anatomical environment of the implanted medical implant, said markers being spatially separated from said medical implant and said markers being different from said x-ray detectable points;
   an x-ray image acquisition apparatus that obtains a first 2D x-ray exposure, from a first projection direction, of a region of the patient containing said implant and said anatomical environment, in which a first distribution of said markers and said points is detectable at a first point in time, and that obtains a second 2D x-ray exposure, from a second 2D x-ray exposure, from a second projection direction different from said first projection direction, of said region at a second point in time, in which a second distribution of said markers and said points is detectable, said second point in time being temporally separated from said first point in time such that a positional change of said implant in said environment may have occurred;
   a device that electronically detects said first and second distributions respectively in said first and second 2D x-ray exposures;
   a computer that calculates from said first and second distributions, with no 3D reconstruction of spatial positions of said markers and points, a degree of probability that said first and second distribution represent projections of the same three-dimensional distribution of said markers and said points and that determines, from said degree of probability, whether a positional change of said implant in said environment has occurred; and
   an output device connected to said computer, said computer being configured to emit a notification, via said output device that identifies only whether said positional change has occurred or not occurred.

8. An x-ray system as claimed in claim 7 wherein said computer determines whether said positional change of the implant has occurred by defining a degree of probability threshold, and automatically electronically generates said indication that a positional change of said implant has occurred if said degree of probability does not exceed said threshold.

9. An x-ray system as claimed in claim 7 wherein said detection device is a digital image processor.

10. An x-ray system as claimed in claim 7 wherein said x-ray image acquisition apparatus at said first point in time, also obtains a first calibrated 2D x-ray exposure of said region, and wherein said computer, from said first 2D x-ray exposure and said first calibrated 2D x-ray exposure, calculates a first 3D distribution of said markers and points for said first point in time, and wherein said x-ray image acquisition apparatus, at said second point in time, obtains a second calibrated 2D x-ray exposure of said region, and wherein said computer, from said second 2D x-ray exposure and said second calibrated 2D x-ray exposure, calculates a second 3D distribution of said markers and said points for said second point in time, and compares said first 3D distribution and said second 3D distribution and, from said comparison, calculates a magnitude of said positional change of said implant, if said position change has occurred.

11. An x-ray system as claimed in claim 7 wherein said implant is a prosthesis, and wherein said plurality of x-ray detectable markers comprises a plurality of metal spheres adapted for placement in at least one bone bordering said implant.

12. An x-ray system as claimed in claim 7 wherein said x-ray detectable points of said implant are x-ray detectable markers introduced into said implant.

* * * * *